United States Patent
Terui et al.

(10) Patent No.: US 9,523,663 B2
(45) Date of Patent: Dec. 20, 2016

(54) MASS SPECTROMETER

(71) Applicant: Hitachi High-Technologies Corporation, Minato-ku, Tokyo (JP)

(72) Inventors: Yasushi Terui, Tokyo (JP); Masaki Yoshie, Tokyo (JP)

(73) Assignee: Hitachi High-Technologies Corporation, Tokyo (JP)

( * ) Notice: Subject to any disclaimer, the term of this patent is extended or adjusted under 35 U.S.C. 154(b) by 0 days.

(21) Appl. No.: 14/908,234

(22) PCT Filed: Jun. 27, 2014

(86) PCT No.: PCT/JP2014/067095
§ 371 (c)(1),
(2) Date: Jan. 28, 2016

(87) PCT Pub. No.: WO2015/015965
PCT Pub. Date: Feb. 5, 2015

(65) Prior Publication Data
US 2016/0169845 A1    Jun. 16, 2016

(30) Foreign Application Priority Data
Aug. 2, 2013   (JP) ................................. 2013-160931

(51) Int. Cl.
*H01J 49/26* (2006.01)
*G01N 30/72* (2006.01)
(Continued)

(52) U.S. Cl.
CPC ........... *G01N 30/7233* (2013.01); *H01J 49/06* (2013.01); *H01J 49/10* (2013.01)

(58) Field of Classification Search
USPC ................................. 250/281, 282, 283, 288
See application file for complete search history.

(56) References Cited

U.S. PATENT DOCUMENTS 6,469,297 B1 * 10/2002  Kato ....................... H01J 49/04
                                                                250/285
2006/0054805 A1    3/2006  Flanagan et al.
(Continued)

FOREIGN PATENT DOCUMENTS

| JP | 2002-8583   A | 1/2002 |
| JP | 2004-303497 A | 10/2004 |

(Continued)

OTHER PUBLICATIONS

International Search Report (PCT/ISA/210) issued in PCT Application No. PCT/JP2014/067095 dated Sep. 16, 2014, with English translation (four (4) pages).

*Primary Examiner* — Nicole Ippolito
(74) *Attorney, Agent, or Firm* — Crowell & Moring LLP

(57) ABSTRACT

The objective of the present invention is to improve the robustness, sensitivity, and maintainability of a mass spectrometer to which a liquid chromatograph can be connected. This mass spectrometer includes: an ion source; a mass spectrometry unit; a plurality of flat plates used as electrodes having openings through which ions can be introduced to the mass spectrometer from an orthogonal direction along an ion introduction axis; a porous member provided between the mass spectrometry unit and the plurality of flat plates; and a mechanism for feeding gas to the plurality of flat plates for the side opposite from the ion introduction direction; the plurality of flat plates being disposed under atmospheric pressure, and the plurality of electrodes being set at a temperature higher than room temperature.

8 Claims, 3 Drawing Sheets

(51) Int. Cl.
*H01J 49/06* (2006.01)
*H01J 49/10* (2006.01)

(56) References Cited

U.S. PATENT DOCUMENTS

| | | |
|---|---|---|
| 2006/0145071 A1 | 7/2006 | Frazer et al. |
| 2008/0067351 A1 | 3/2008 | Satoh et al. |
| 2010/0044558 A1* | 2/2010 | Sudakov ............... H01J 49/406 250/281 |
| 2011/0192969 A1 | 8/2011 | Verentchikov |
| 2012/0161029 A1 | 6/2012 | Makarov et al. |
| 2014/0224982 A1* | 8/2014 | Furuhashi ............. H01J 49/403 250/287 |
| 2015/0034814 A1* | 2/2015 | Brown ................. H01J 49/164 250/282 |
| 2015/0179421 A1* | 6/2015 | Jarrell .................. H01J 49/405 250/505.1 |

FOREIGN PATENT DOCUMENTS

| | | |
|---|---|---|
| JP | 2006-86124 A | 3/2006 |
| JP | 2007-287404 A | 11/2007 |
| JP | 2011-258563 A | 12/2011 |
| JP | 2011-529623 A | 12/2011 |
| JP | 2012-114096 A | 6/2012 |
| WO | WO 2013/005059 A1 | 1/2013 |

\* cited by examiner

2000: ATMOSPHERIC ION INTRODUCTION ELECTRODE, RF VOLTAGE OFF

2010: ATMOSPHERIC ION INTRODUCTION ELECTRODE, RF VOLTAGE ON

MASS SPECTROMETER

TECHNICAL FIELD

The present invention relates to a mass spectrometer to which a liquid chromatograph can be connected.

BACKGROUND ART

A liquid chromatograph (LC) becomes an analysis device necessary for researching and developing organic chemistry and is introduced widely in laboratories at universities, laboratories in chemical companies and the like. In the natural world, materials of single components are little and most of materials are mixtures of complex components. The liquid chromatograph is a device that can separate the complex components into individual components, using a liquid as a measurement sample. The complex components are separated into the individual components, so that calculation of a content of each component and extraction and elimination of a specific component are enabled. When these components are detected, types of measured samples may be large and detectors for the liquid chromatograph may be diversified. Even as for detectors to which representative optical technology is applied, there are an ultraviolet detector, a visible detector, a diode array detector, a differential refractive index detector, an electric conductivity detector, a fluorescent detector, and a chemiluminescence detector.

In addition, when molecular weights of the components separated by the liquid chromatograph are measured, a mass spectrometer (MS) is used. A device to which the liquid chromatograph and a mass spectrometry unit are coupled is called a liquid chromatograph/mass spectrometer (LC/MS). The mass spectrometer ionizes a sample solution and introduces the ions into the mass spectrometer in at vacuum state. The mass spectrometer separates the ions by electric and magnetic actions according to a mass/charge ratio (m/z) and detects the individual ions. A mass spectrum in which a horizontal axis shows the mass/charge ratio and a vertical axis shows detection strength is obtained. Because a charged component (ion) molecule is directly detected, sensitivity is high as compared with the detector using the optical technology. In addition, there is a superior characteristic in that a structure of the component can be determined because the molecular weight can be measured. For this reason, the liquid chromatograph/mass spectrometer is used in wide fields such as development and quality control of pharmaceutical products, environment measurement, and foods. Recently, measurement of a blood biomarker from the knowledge obtained from a biomarker search, measurement of protein generated from genetic information, and structure analysis of the protein after a modification in a cell attract attention.

A use environment of the liquid chromatograph/mass spectrometer also spreads from the university or company laboratories to clinical laboratories in hospitals and the liquid chromatograph/mass spectrometer changes from a device used by a specialist in mass spectrometry to a device used by a specialist in other field. For this reason, a device that has convenience and high durability as well as high sensitivity to be one of characteristics of the mass spectrometry and a device that can perform maintenance easily are demanded.

The mass spectrometers are largely divided into devices mainly performing quantitative analysis and devices mainly performing qualitative analysis. As a representative mass spectrometer that mainly performs the quantitative analysis, there is a triple quadrupole mass spectrometer (hereinafter, referred to as the triple-QMS) that has a plurality of quadrupole mass spectrometry units provided inside. Because the triple-QMS has a characteristic that specific ions of a measurement sample can be continuously detected, quantitative analysis performance is high. Meanwhile, as a mass spectrometer that mainly performs the qualitative analysis, there is a flight time type mass spectrometry unit (hereinafter, referred to as the TOF/MS). Measurement ions are flown in vacuum, a time until the ions arrive at a detector is measured, and a molecular weight is measured. Because a width of a mass/charge ratio observed is large and a mass spectrum with high resolution is easily obtained, qualitative analysis performance becomes high.

In the mass spectrometer, an internal state becomes a vacuum state, electrodes having various shapes are disposed, and ions introduced into the mass spectrometer are controlled and separated by an electric field. For example, the quadrupole mass spectrometry unit is also called a Q mass (QMF) or a mass filter and includes four cylindrical electrodes. The cylindrical electrodes are combined by positioning a center of a circle at a vertex of a square. A positive/negative direct current and a high frequency alternating-current voltage are applied to the electrodes adjacent to the fixed cylindrical electrode to be superimposed. When the ions having the charge pass through the electrodes, the ions pass through the electrodes while vibrating and only a certain ion vibrates stably according to the voltage and the frequency and passes through the electrodes. Meanwhile, the vibration of the other ions increases during passing through the electrodes and the ions collide the electrodes and cannot pass through the electrodes. The mass spectrum is obtained by changing the high frequency alternating-current voltage linearly while maintaining a ratio of the direct current and the alternating-current voltage constantly.

A device in which one quadrupole mass spectrometry unit (QMF) is mounted in the mass spectrometer is called a single quadrupole mass spectrometer (hereinafter, referred to as the Single-QMS). Because the mass spectrometer has a small size, the mass spectrometer is relatively cheap and is used widely for gas analysis. Meanwhile, the resolution of the mass spectrum is not high as about a 1 mass-charge ratio width. In addition, when the mass spectrometer is used as the detector of the liquid chromatograph, sensitivity is deteriorated because a noise derived from the solvent is observed at a low mass-charge ratio.

CITATION LIST

Patent Literature

PTL 1: Japanese Patent Application Laid-Open. No. 2011-258563

SUMMARY OF INVENTION

Technical Problem

As representative mass spectrometers coupled for the quantitative analysis in the liquid chromatograph/mass spectrometer, there are the Single-QMS and the Triple-QMS. As a name suggests, a typical Triple-QMS mounts three QMFs inside, transmits only a specific ion (A) by the first QMF, decomposes (A') the ion by the second QMF, and detects the decomposed ion (A') by the third QMF. This measurement method is called an MSMS method. The Single-QMS mounts one QMF inside and detects a specific ion (A). (A plurality of ions can be detected by changing an observation ion temporally). One of differences of the Triple-QMS and the Single-QMS is whether the MSMS method is enabled or disabled. When a noise ion (B) having almost the same mass as the mass of the specific ion (A) selected by the first QMF is superimposed on the specific ion (A), the specific ion (A) and the noise ion (B) are added (A+B) and observed, due to low resolution of the QMF. However, in a lot of cases, structures of the specific ion (A) and the noise ion (B) are different from each other. For this reason, if the ions are decomposed, mass/charge ratios of the decomposed specific ion. (A') and the decomposed noise ion (B') are different from each other. Only the mass/charge ratio of the decomposed specific ion (A') is observed, so that only the specific ion can be selectively decomposed. This is because the noise can be reduced by detecting only the specific ion (A') after the decomposition, at the time of the quantitative analysis of the specific ion (A), and SN can be greatly improved. Because the MSMS analysis is disabled in the Single-QMS, the noise cannot be reduced and the sensitivity of the Single-QMS is disadvantageous as compared with the Triple-QMS.

As representative noises observed in the liquid chromatograph/mass spectrometer, there are a solvent-derived ion of a liquid introduced into the mass spectrometer, a noise observed when a neutral particle not to be charged collides with the detector in the mass spectrometer, and a noise generated from the detector. An object of the invention is to reduce solvent-derived ions of an introduced liquid and realize high sensitivity, in a mass spectrometer.

In addition, because the mass spectrometer operates ions by a magnetic field and an electric field in the mass spectrometer, an internal state of the mass spectrometer becomes a vacuum state. For example, when an inner portion of the mass spectrometer is polluted by a measurement sample, it is necessary to stop a vacuum and perform maintenance and a long time is necessary to stop the vacuum, perform the maintenance, and restart the vacuum in the mass spectrometer. The specialized knowledge is necessary for the maintenance and it is required to perform pollution control measures of the mass spectrometer at the atmospheric side (the vacuum is not stopped).

Solution to Problem

To solve the problem, a mass spectrometer of the present invention includes:
an ion source;
a mass spectrometry unit;
a plurality of flat plates which function as electrodes having openings through which ions are introduced in a direction orthogonal to an ion introduction axis for the mass spectrometer;
a porous member which is provided between the mass spectrometry unit and the plurality of flat plates; and
a mechanism which flows gas to the plurality of flat plates for the side opposite to the ion introduction direction,
wherein the plurality of flat plates are disposed under atmospheric pressure and temperatures of the plurality of electrodes are set to temperatures higher than a room temperature.

Advantageous Effects of Invention

According to the invention, in a mass spectrometer that can be connected to a liquid chromatograph, neutral particles not ionized at the time of ionizing and low molecular ions derived from a solvent used in the liquid chromatograph, which are main components of noise components, are reduced and sensitivity of the mass spectrometer is improved. At the same time, because pollution occurring when a liquid sample is measured by the mass spectrometer is detected at the atmospheric side, maintenance of the mass spectrometer can be performed under atmospheric pressure and the maintenance becomes easy.

DESCRIPTION OF EMBODIMENTS

Figure 1:
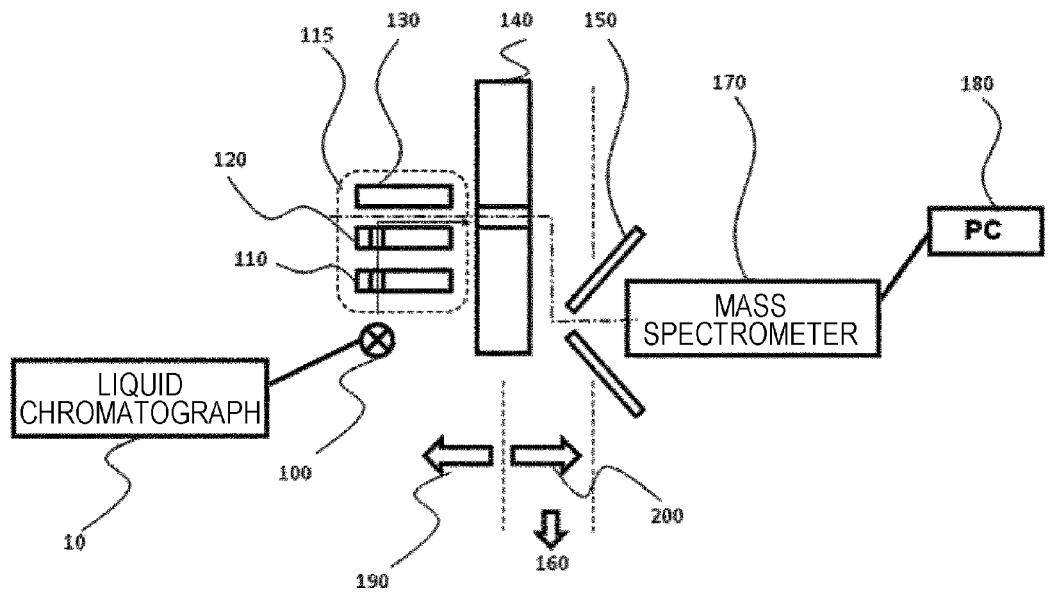
FIG. 1 illustrates an example of a configuration of a mass spectrometer in the present invention.
Figure 2:
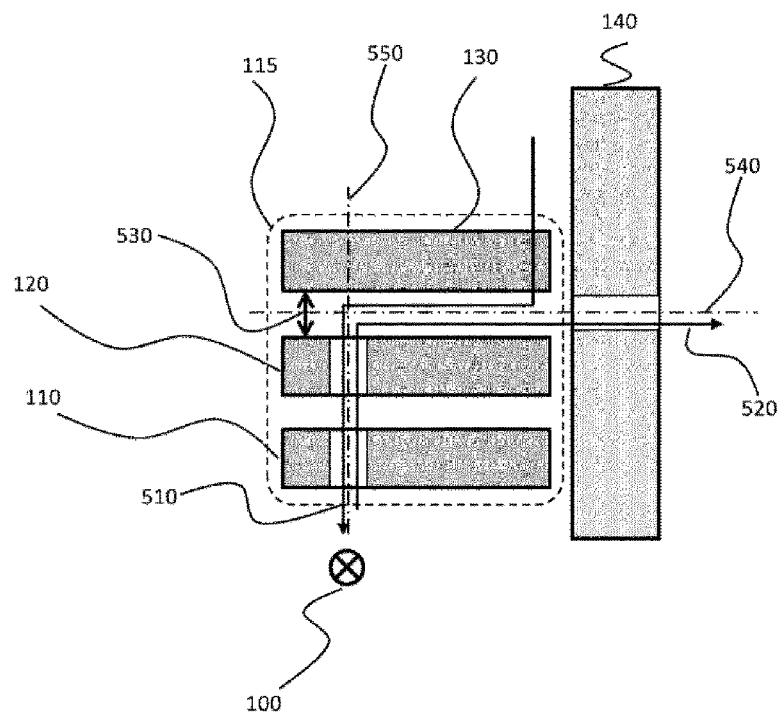
FIG. 2 illustrates the detail of a configuration of an atmospheric ion introduction electrode in the present invention.
Figure 3:
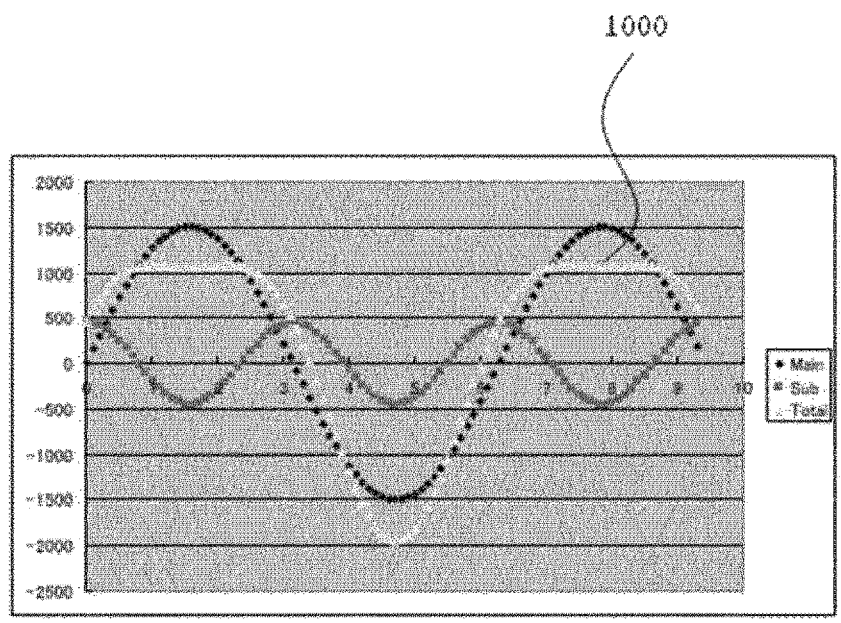
FIG. 3 illustrates an example of an RF voltage applied to the atmospheric ion introduction electrode in the present invention.
Figure 3:
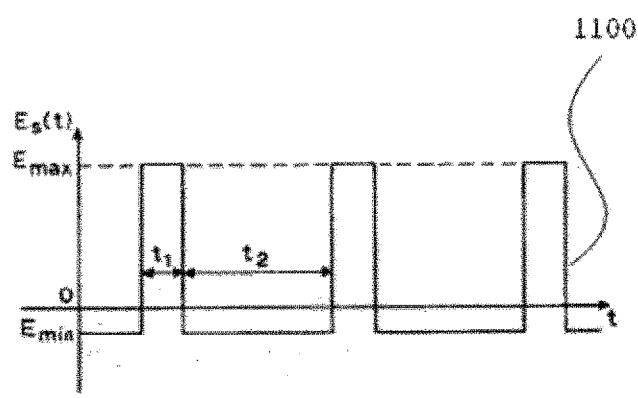

FIG. 2 illustrates an example of a configuration of an atmospheric ion introduction electrode according to an embodiment of the present invention.

Embodiment

A measurement sample fed by a liquid chromatograph 10 and the like is ionized by an ion source 100. The ion source 100 is under atmospheric pressure. Ions generated from the ion source 100 are introduced into an atmospheric ion introduction electrode unit 115. The atmospheric ion introduction electrode 115 is configured by a plurality of parallel flat plates. In this embodiment, three parallel flat plates are illustrated. The ions having passed through a slit of a counter electrode 110 pass through a slit in a front electrode 120 and are introduced into a gap between the front electrode 120 and a rear electrode 130 connected to an ion introduction opening of a mass spectrometer. At this time, absolute values of voltages applied to the counter electrode 110, the front electrode 120, and the rear electrode 130 are set as counter electrode 110>=front electrode 120>=rear electrode 130, so that ion introduction efficiency in the mass spectrometer can be improved. The ions having passed through the gap between the front electrode 120 and the rear electrode 130 enter a first pore 140 of a mass spectrometry unit.

The first pore 140 becomes a partition wall between an atmospheric side 190 and a vacuum side 200 and a vacuum is created between the first pore 140 and a second pore 150 by connecting (160) a vacuum pump such as a rotary pump. The ions having passed through the second pore 150 are introduced into a single quadrupole mass spectrometry unit (Single QMS) 170, for example. The mass spectrometry unit 170 to execute mass separation of the ions may be a quadrupole mass spectrometry unit, an ion trap, a flight time type, a Fourier transform type, or the like. The mass spectrometry unit is connected to a PC 180 to execute control of the mass spectrometer and data processing and obtains data.

FIG. 2 illustrates the detail of the atmospheric ion introduction electrode unit 115. The atmospheric ion introduction electrode 115 is configured by a plurality of parallel flat plates. In this embodiment, three parallel flat plates are illustrated. The ions generated by the ion source 100 are introduced into the first pore 140 of the mass spectrometer along an ion flow 520. Meanwhile, gas can be flown to the atmospheric ion introduction electrode 115 and a gas flow 510 is generated in a direction facing the ion flow 520. A diameter of the first pore 140 of the mass spectrometer is about ϕ0.3. The gap between the front electrode 120 and the rear electrode 130 has a shape of a parallel flat plate, an interval 530 of the front electrode 120 and the rear electrode 130 is 2 mm or less, an area of the gap is larger than an area of the first pore 140, and the gas easily flows. For this reason, most of the introduced gas flow 510 passes through the gap between the front electrode 120 and the rear electrode 130 and flows in a direction toward the counter electrode 510. The gap of the front electrode 120 and the rear electrode 130 may be 1 mm or less.

In the ion source 100, the ions are basically generated. However, the sprayed gas includes neutral particles that cannot be ionized, droplets that have large particle diameters and the like in addition to the ions. The gas flow 510 discharged from the counter electrode 510 prevents the neutral particles, the large droplets and the like from entering the mass spectrometer. Meanwhile, a flow rate of the gas flowing between the front electrode 120 and the rear electrode 130 is about 2.0 L/min or less and is faster than a flow rate of the gas sprayed from the ion source 100. Even though the neutral particles pass through the counter electrode 110, the neutral particles cannot pass through the gap between the front electrode 120 and the rear electrode 130. Because the ions are the charged particles as the name suggests, absolute values of voltages electrically applied to the counter electrode 110, the front electrode 120, and the rear electrode 130 are set as counter electrode 110>=front electrode 120>=rear electrode 130, so that the ions are introduced into the side of the mass spectrometry unit 170.

In addition, the atmospheric ion introduction electrode 115 has an opening through which the ions can be introduced in a direction orthogonal to an ion introduction axis for the mass spectrometry unit 170. The neutral particles having the large particle diameters collide with the rear electrode 130, so that the neutral particles are prevented from being introduced into the mass spectrometry unit 170.

In addition, temperatures of the electrodes configuring the atmospheric ion introduction electrode unit 115 are set to be higher than a room temperature and to be equal to or lower than about 250° C., so that ionizing can be accelerated in the atmospheric ion introduction electrode 115.

As described above, most of the ions passing through the gap between the front electrode 120 and the rear electrode 130 have the charge, from the structure of the atmospheric ion introduction electrode unit 115, the gas flow, and the temperature setting. For this reason, an electric operation is enabled in the atmospheric pressure (a mean free path is short). An RF component 1000 in which a positive component and a negative component are asymmetrical is applied to the rear electrode 130; and a direct-current voltage necessary for ion introduction is applied to the front electrode 120. Then, the ions are operated within the gap of the shape of the parallel flat plate between the front electrode 120 and the rear electrode 130. The RE signal may be applied to only the front electrode 120 or both the front electrode 120 and the rear electrode 130. This is because a voltage of a direct-current component is superimposed on each RE signal, so that the ion operation and the ion introduction for the mass spectrometry unit 170 are enabled. In addition, the applied RF signal is not a sine wave and may be a rectangular wave 1100 and a triangular wave. Here, amplitude of the asymmetrical RF voltage can be set differently in a solvent used by the liquid chromatograph and a sample of a measurement target.

A representative diameter of the first pore of the mass spectrometer is about ϕ0.3 to 0.5 mm. For this reason, the ions passing through the gap of the shape of the parallel flat plate between the front electrode 120 and the rear electrode 130 are slightly moved, so that the ions may be introduced or not introduced into the mass spectrometer.

Meanwhile, in the liquid chromatograph, the measurement sample is the liquid and the used representative solvent is water, methanol, and acetonitrile. There is hardly any demand for measuring these solvents because they are originally "a s solvent". If the solvent, is ionized and is introduced into the mass spectrometer, the ions become a noise source and causes sensitivity of the mass spectrometer to be deteriorated. For this reason, if an amount of low molecular ions, derived from the solvent, introduced into the mass spectrometry unit 170 is decreased, the noise decreases and the sensitivity of the mass spectrometer is improved.

In a liquid chromatograph/mass spectrometry unit, there are various types of measurement targets. However, there are steroids such as testosterone as a representative measurement sample. The steroid has a benzene ring structure inside and the structure thereof is different from structures of linear molecules such as water, methanol, and acetonitrile to be the solvents. Because the behaviors of the ions passing through the gap of the shape of the parallel flat plate between the front electrode 120 and the rear electrode 130 are defined by mobility of the ions, the mobility is different according to the molecular structure. For this reason, the solvent and the measurement sample can be divided by the applied voltage.

Figure 4:
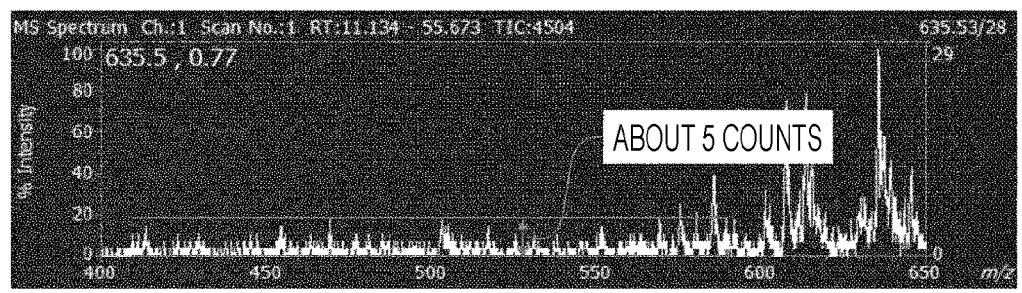
FIG. 4 illustrates an operation of the atmospheric ion introduction electrode in the present invention and a mass spectrum difference according to ON/OFF.
Figure 4:
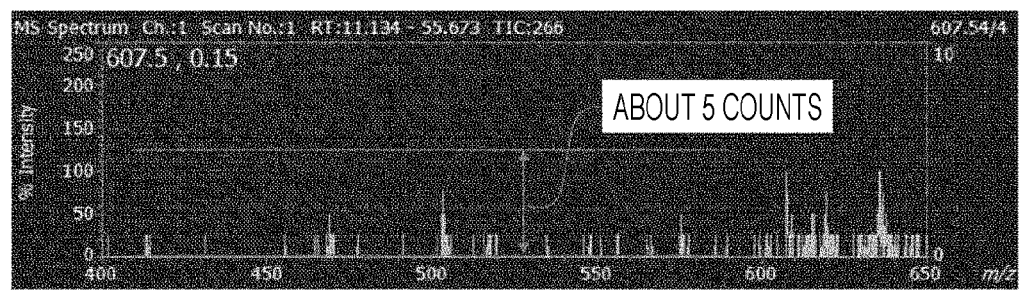

Therefore, the voltages are set such that the ions derived from the solvent introduced from the liquid chromatograph do not pass through the gap of the shape of the parallel flat plate between the front electrode 120 and the rear electrode 130 and the measurement ions pass through the gap, at the time of passing through the gap, so that the amount of low molecular ions, derived from the solvent, introduced into the mass spectrometer can be decreased. In 2000 and 2100 of FIG. 4, data when the RF is not applied to the atmospheric ion introduction electrode unit and data when the RF is applied to the atmospheric ion introduction electrode unit are illustrated, respectively. A horizontal axis shows a mass/charge ratio and a vertical axis shows signal strength. When the RF of the atmospheric ion introduction electrode unit is set to Off, a noise of about 5 counts is observed as a background. If the RF is set to On, a background component becomes 1 to 2 counts and the noise becomes about ½ to ⅕. Because signal strength of a target component is rarely changed and is observed, SN is improved about 2 to 5 times.

When the solvent and the like are measured, the application of the RF voltage to the atmospheric ion introduction electrode unit can be set to Off.

Because the atmospheric ion introduction electrode according to the present invention is connected to the atmospheric side of the mass spectrometry unit, the atmospheric ion introduction electrode can be adopted in the Single QMS, the Triple QMS, an ion trap, a flight time type, a Fourier transform type, or a complex type mass spectrometer. The sensitivity of the mass spectrometer is improved due to reduction of the noise. Particularly, the atmospheric ion introduction electrode is introduced into the Single QMS in which the MSMS analysis is disabled, so that a reduction effect of the noise is large, and maintenance is enabled under the atmospheric pressure. Therefore, even if there is not specialized knowledge, the present invention can be carried out.

REFERENCE SIGNS LIST 10 liquid chromatograph
100 ion source
110 counter electrode
115 atmospheric ion introduction electrode
120 front electrode
130 rear electrode
140 first pore
150 second pore
160 connection with vacuum pump
170 mass spectrometry unit
180 device control and data processing apparatus such as PC
190 atmospheric side
200 vacuum side
510 gas flow
520 ion flow
530 distance between front electrode 120 and rear electrode 130
540 ion introduction axis in mass spectrometer
550 ion introduction axis in mass spectrometer
1000 voltage setting example (sine wave shape) of rear electrode 130
1100 voltage setting example (rectangular wave shape) of rear electrode 130
2000 atmospheric ion introduction electrode unit, RF voltage OFF
2100 atmospheric ion introduction electrode unit, RF voltage ON

The invention claimed is:

1. A mass spectrometer, comprising:
an ion source;
a mass spectrometry unit;
a plurality of flat plates which function as electrodes having openings through which ions are introduced in a direction orthogonal to an ion introduction axis for the mass spectrometer;
a porous member which is provided between the mass spectrometry unit and the plurality of flat plates; and
a mechanism which flows gas to the plurality of flat plates for the side opposite to the ion introduction direction,
wherein the plurality of flat plates are disposed under atmospheric pressure and temperatures of the plurality of electrodes are set to temperatures higher than a room temperature.

2. The mass spectrometer according to claim 1, wherein the two flat plates of the plurality of flat plates are disposed such that a gap thereof faces a pore provided in the porous member and a diameter of the pore is smaller than an interval of the two flat plates.

3. The mass spectrometer according to claim 2, wherein the interval of the two flat plates is 2 mm or less.

4. The mass spectrometer according to claim 1, wherein a flow rate of the gas of the mechanism which flows the gas is 2.0 L/min or less.

5. The mass spectrometer according to claim 1, wherein electrode temperatures of the plurality of flat plates are equal to or lower than 250° C.

6. A mass spectrometer, comprising:
an ion source;
a mass spectrometry unit;
a plurality of flat plates which function as electrodes having openings through which ions are introduced in a direction orthogonal to an ion introduction axis for the mass spectrometer; and
a porous member which is provided between the mass spectrometry unit and the plurality of flat plates,
wherein absolute values of direct-current voltages applied to the plurality of flat plates decrease toward the side of the mass spectrometry unit from the side of the ion source or are the same as an absolute value of one flat plate of the side of the ion source.

7. A mass spectrometer, comprising:
an ion source;
a mass spectrometry unit;
a plurality of flat plates which function as electrodes having openings through which ions are introduced in a direction orthogonal to an ion introduction axis for the mass spectrometer; and
a porous member which is provided between the mass spectrometry unit and the plurality of flat plates,
wherein the two flat plates of the plurality of flat plates are disposed such that a gap thereof faces a pore provided in the porous member and an RF voltage in which a positive component and a negative component are asymmetrical is applied to at least one of the two flat places.

8. The mass spectrometer according claim 7, wherein amplitude of the RF voltage to be asymmetrical is different in a solvent used by a liquid chromatograph and a sample of a measurement target.

* * * * *